(12) United States Patent
Kelly

(10) Patent No.: US 11,096,664 B2
(45) Date of Patent: Aug. 24, 2021

(54) SYSTEM AND METHOD FOR PERFORMING AN ULTRASOUND SCAN OF CELLULAR TISSUE

(71) Applicant: SONOCINE, INC., Reno, NV (US)

(72) Inventor: Kevin M. Kelly, Venice, CA (US)

(73) Assignee: SONOCINE, INC., Reno, NV (US)

( * ) Notice: Subject to any disclaimer, the term of this patent is extended or adjusted under 35 U.S.C. 154(b) by 0 days.

(21) Appl. No.: 16/833,879

(22) Filed: Mar. 30, 2020

(65) Prior Publication Data

US 2020/0222028 A1  Jul. 16, 2020

Related U.S. Application Data

(62) Division of application No. 14/665,956, filed on Mar. 23, 2015, now Pat. No. 10,603,010.

(Continued)

(51) Int. Cl.
*A61B 8/00* (2006.01)
*A61B 8/14* (2006.01)
(Continued)

(52) U.S. Cl.
CPC .......... *A61B 8/4444* (2013.01); *A61B 8/4209* (2013.01); *A61B 8/4218* (2013.01);
(Continued)

(58) Field of Classification Search
CPC ... A61B 8/4444; A61B 8/4209; A61B 8/4218; A61B 8/4245; A61B 8/14; A61B 8/5207; A61B 8/0825; A61B 8/40; A61B 6/0407
(Continued)

(56) References Cited

U.S. PATENT DOCUMENTS 3,480,002 A 11/1969 O'Connor
4,206,763 A 6/1980 Pedersen
(Continued)

FOREIGN PATENT DOCUMENTS

CN 201939377 8/2011
DE 3227624 1/1984
JP 2008272409 11/2008

OTHER PUBLICATIONS

Abe, Hiroyuki, et al. US-guided Core Needle Biopsy of Axillary Lymph Nodes in Patients with Breast Cancer: Why and How to Do It [online]. RadioGraphics, 2007 [retrieved on Mar. 12, 2019], vol. 27, pp. S91-S99. Retrieved from the Internet: <URL: https:// pubs .rsna .org/doi/10 .1148/rg .27si 07 5502> <DOI: see office action>.

(Continued)

*Primary Examiner* — Carolyn A Pehlke
*Assistant Examiner* — Victoria Fang

(57) ABSTRACT

A method of performing an ultrasound scan of cellular tissue by placing a flexible membrane overlaid with ultrasonic coupling material as part of a probe enclosure adjacent the cellular tissue, pressurizing the probe enclosure, moving an ultrasound probe within the probe enclosure over the flexible membrane with the head of the ultrasound probe submerged in the ultrasonic coupling material and displaced from the flexible membrane and generating a plurality of cross-sectional images of the cellular tissue as the ultrasound probe moves over the flexible membrane. The ultrasonic probe may be driven by a programmable controller. A flat surface of an axilla pad may be placed adjacent the flexible membrane and an examination wedge may be placed under one lateral side of a patient to raise the one lateral side of the patient above the other lateral side of the patient when the flexible membrane is placed adjacent to the cellular tissue.

9 Claims, 13 Drawing Sheets

Related U.S. Application Data

(60) Provisional application No. 61/968,712, filed on Mar. 21, 2014.

(51) Int. Cl.
  *A61B 8/08* (2006.01)
  *A61B 6/04* (2006.01)

(52) U.S. Cl.
  CPC ........... *A61B 6/0407* (2013.01); *A61B 8/0825* (2013.01); *A61B 8/14* (2013.01); *A61B 8/40* (2013.01); *A61B 8/4245* (2013.01); *A61B 8/5207* (2013.01)

(58) Field of Classification Search
  USPC ........................................................ 600/443
  See application file for complete search history.

(56) References Cited

U.S. PATENT DOCUMENTS

| | | |
|---|---|---|
| 2003/0125623 A1 | 7/2003 | Kelly et al. |
| 2004/0081273 A1 | 4/2004 | Ning |
| 2006/0173304 A1 | 8/2006 | Wang |
| 2007/0027390 A1 | 2/2007 | Maschke et al. |
| 2007/0092059 A1 | 4/2007 | Wayne et al. |
| 2007/0239020 A1 | 10/2007 | Iinuma et al. |
| 2008/0242979 A1 | 10/2008 | Fisher et al. |
| 2010/0063396 A1 | 3/2010 | Anderson et al. |
| 2010/0125198 A1 | 5/2010 | Thapliyal et al. |
| 2012/0022376 A1 | 1/2012 | Amara et al. |
| 2012/0029358 A1 | 2/2012 | Lin |
| 2014/0121520 A1 | 5/2014 | Wang et al. |
| 2015/0031998 A1 | 1/2015 | Kyono et al. |

OTHER PUBLICATIONS

Orange Aid(R) Gel Pads and Positioners [online]. Mizuhosi, Nov. 28, 2013 [retrieved on Mar. 12, 2019]. Retrieved from the Internet: <URL:https://web.archive.org/web/20131128023619/https://mizuhosi.com/products/pressure-management/orange-aid-gel-pads-and-positioners/orange-aid-universal-patient-positioners/>.

International Search Report and Written Opinion for PCT/US2015/022040 dated Jun. 29, 2015.

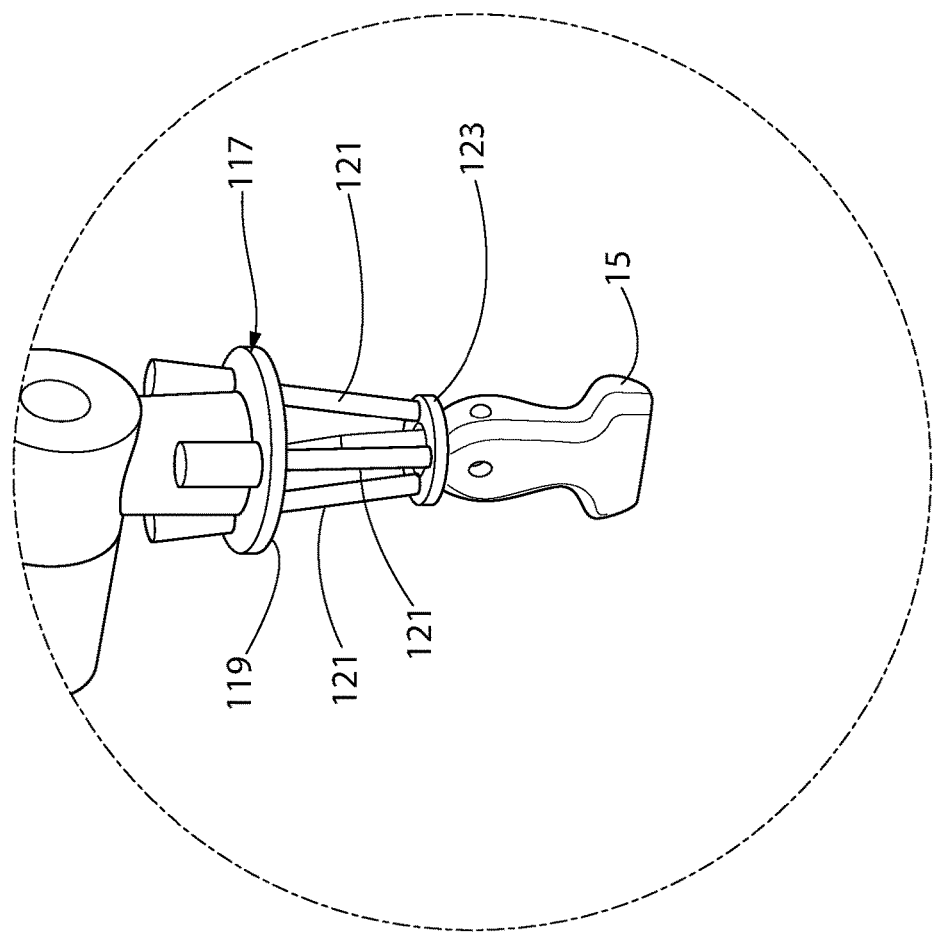
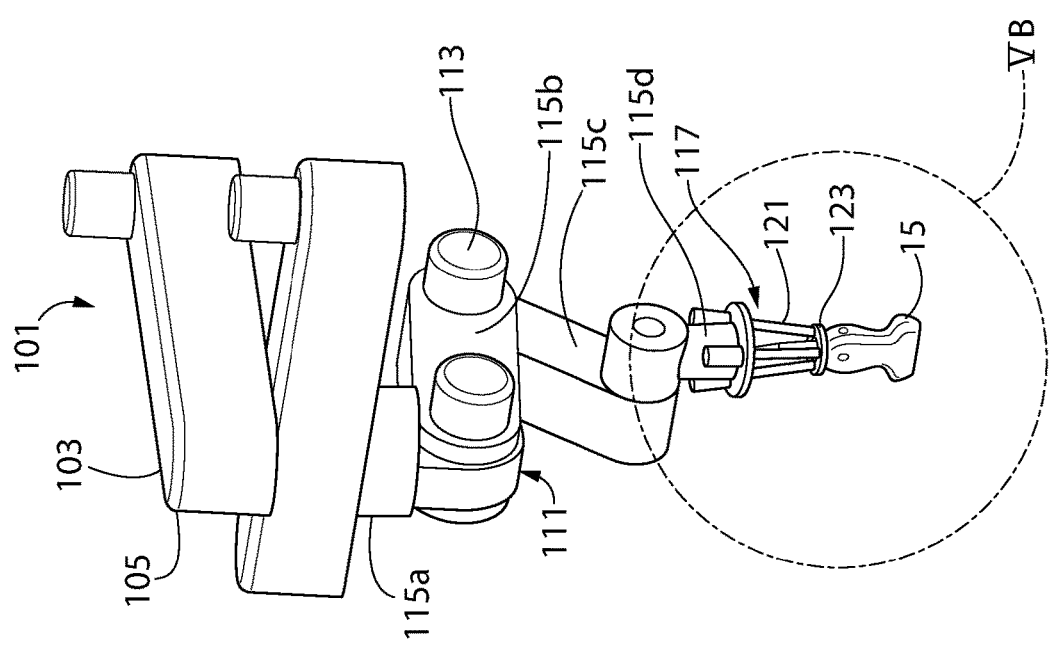
FIG. 5A
FIG. 5B

SYSTEM AND METHOD FOR PERFORMING AN ULTRASOUND SCAN OF CELLULAR TISSUE

CROSS REFERENCE TO RELATED APPLICATIONS

Priority is claimed as a divisional application to U.S. patent application Ser. No. 14/665,956, filed Mar. 23, 2015, which claims priority to U.S. provisional patent application No. 61/968,712, filed Mar. 21, 2014, the disclosure of which is incorporated herein by reference in its entirety.

FIELD OF THE INVENTION

The field of the present invention relates to ultrasonic scanning and diagnostics for cellular tissue.

BACKGROUND OF THE INVENTION

Ultrasound as an independent screening tool for diagnosing cancers, particularly in breast tissue, is becoming more widely recognized and accepted within the medical community. Historically, in the context of breast exams and breast cancers, ultrasound was first used to diagnose breast cancers if the location of the abnormality is first discovered by another modality, such as mammography or physical examination. Recently, ultrasound as a stand-alone diagnostic tool for breast cancers has become more widely accepted based on the development of technology that enables ultrasound to be used to screen the entire breast tissue and have an acceptably high success rate in finding abnormalities that may be cancerous. One system that has been developed to uniformly and reliably screen tissues, such as breast tissue, for cancer uses ultrasound probes to create a contiguous and complete set of scan images for the entire area of the tissue being screened. One such system is described in U.S. Pat. No. 6,524,246, the disclosure of which is incorporated herein by reference in its entirety.

One of the limitations of such a system is the amount of time needed to perform the scans. Even though such a system may automate the acquisition of ultrasound images, the process can still be somewhat slow, especially when compared to other breast tissue screening methods, such as mammography. Another limitation with present ultrasound systems is that they all rely on the ultrasound probe coming into contact with the surface of the tissue being screened. This contact causes deformation of the tissue, and deformation of the tissue can cause difficulties for identifying abnormalities when the ultrasound images are being viewed.

SUMMARY OF THE INVENTION

The present invention is directed toward a system and method for performing an ultrasound scan of cellular tissue. In performing the ultrasound scan, a probe enclosure having a flexible membrane forming one side is placed with the flexible membrane adjacent the cellular tissue. The probe enclosure houses both an ultrasound probe and an ultrasonic coupling material, and the ultrasound scan is performed by moving the ultrasound probe within the probe enclosure with the head of the ultrasound probe submerged in the ultrasonic coupling material.

In a first separate aspect of the present invention, a system for performing an ultrasound scan of cellular tissue includes: an ultrasound scanning device including an ultrasound probe, the ultrasound scanning device configured to generate cross-sectional images of the cellular tissue; a probe enclosure in which the ultrasound probe is disposed, wherein a side part of the probe enclosure is formed by a flexible membrane, the probe enclosure is configured to hold an ultrasonic coupling material on the flexible membrane, the flexible membrane and the ultrasonic coupling material being ultrasonically conductive, and a the probe enclosure forms a cavity adjacent the flexible membrane, the cavity being configured to be pressurized above atmospheric pressure; an armature is configured to support the probe enclosure and to move the probe enclosure into a position where the flexible membrane is placed adjacent to and displaced by the cellular tissue; a probe positioning assembly configured to support the ultrasound probe within the probe enclosure and to move the ultrasound probe over the flexible membrane with a head of the ultrasound probe submerged in the ultrasonic coupling material, the ultrasound scanning device generating the cross-sectional images of the cellular tissue as the probe positioning assembly progressively moves the ultrasound probe over the flexible membrane, wherein the probe positioning assembly includes at least one sensor configured to measure a position of the probe within the probe enclosure; and a controller operatively coupled to the probe positioning assembly, wherein the controller is programmed to control movement of the ultrasound probe in response to measurements by the at least one sensor.

In a second separate aspect of the present invention, a system for performing an ultrasound scan of cellular tissue includes: an ultrasound scanning device including an ultrasound probe, the ultrasound scanning device configured to generate cross-sectional images of the cellular tissue; a probe enclosure in which the ultrasound probe is disposed, wherein a side part of the probe enclosure is formed by a flexible membrane, the probe enclosure is configured to hold an ultrasonic coupling material on the flexible membrane, the flexible membrane and the ultrasonic coupling material being ultrasonically conductive, and a the probe enclosure forms a cavity adjacent the flexible membrane, the cavity being configured to be pressurized above atmospheric pressure; an armature is configured to support the probe enclosure and to move the probe enclosure into a position where the flexible membrane is placed adjacent to and displaced by the cellular tissue; a probe positioning assembly configured to support the ultrasound probe within the probe enclosure and to move the ultrasound probe over the flexible membrane with a head of the ultrasound probe submerged in the ultrasonic coupling material, the ultrasound scanning device generating the cross-sectional images of the cellular tissue as the probe positioning assembly progressively moves the ultrasound probe over the flexible membrane, wherein the probe positioning assembly includes at least one sensor configured to measure a position of the probe within the probe enclosure; and a controller operatively coupled to the probe positioning assembly, wherein the controller is programmed to control movement of the ultrasound probe in response to measurements by the at least one sensor.

In a third separate aspect of the present invention, a method of performing an ultrasound scan of cellular tissue includes: placing a probe enclosure adjacent the cellular tissue, wherein an ultrasound probe and an ultrasonic coupling material are disposed within the probe enclosure and a bottom of the probe enclosure is formed by a flexible membrane, the flexible membrane and the ultrasonic coupling material being ultrasonically conductive, and wherein the flexible membrane is placed adjacent to and displaced by the cellular tissue; pressurizing a cavity formed by the probe enclosure, the cavity being adjacent the flexible membrane;

moving the ultrasound probe within the probe enclosure over the flexible membrane, such that a head of the ultrasound probe is maintained at least at a minimum distance from the flexible membrane; and generating a plurality of cross-sectional images of the cellular tissue as the probe positioning assembly progressively moves the ultrasound probe over the flexible membrane.

Accordingly, an improved system and method for performing an ultrasound scan of cellular tissue are disclosed. Advantages of the improvements will be apparent from the drawings and the description of the preferred embodiment.

BRIEF DESCRIPTION OF THE DRAWINGS

The foregoing summary, as well as the following detailed description of the exemplary embodiments, will be better understood when read in conjunction with the appended drawings. It should be understood, however, that the invention is not limited to the precise arrangements and instrumentalities shown in the following figures:

FIG. 5A is a perspective view of a probe positioning assembly for an ultrasound scanning system;

FIG. 5B is a detailed view of the probe support for the probe positioning assembly of FIG. 5A;

DETAILED DESCRIPTION OF THE INVENTION

Figure 1:
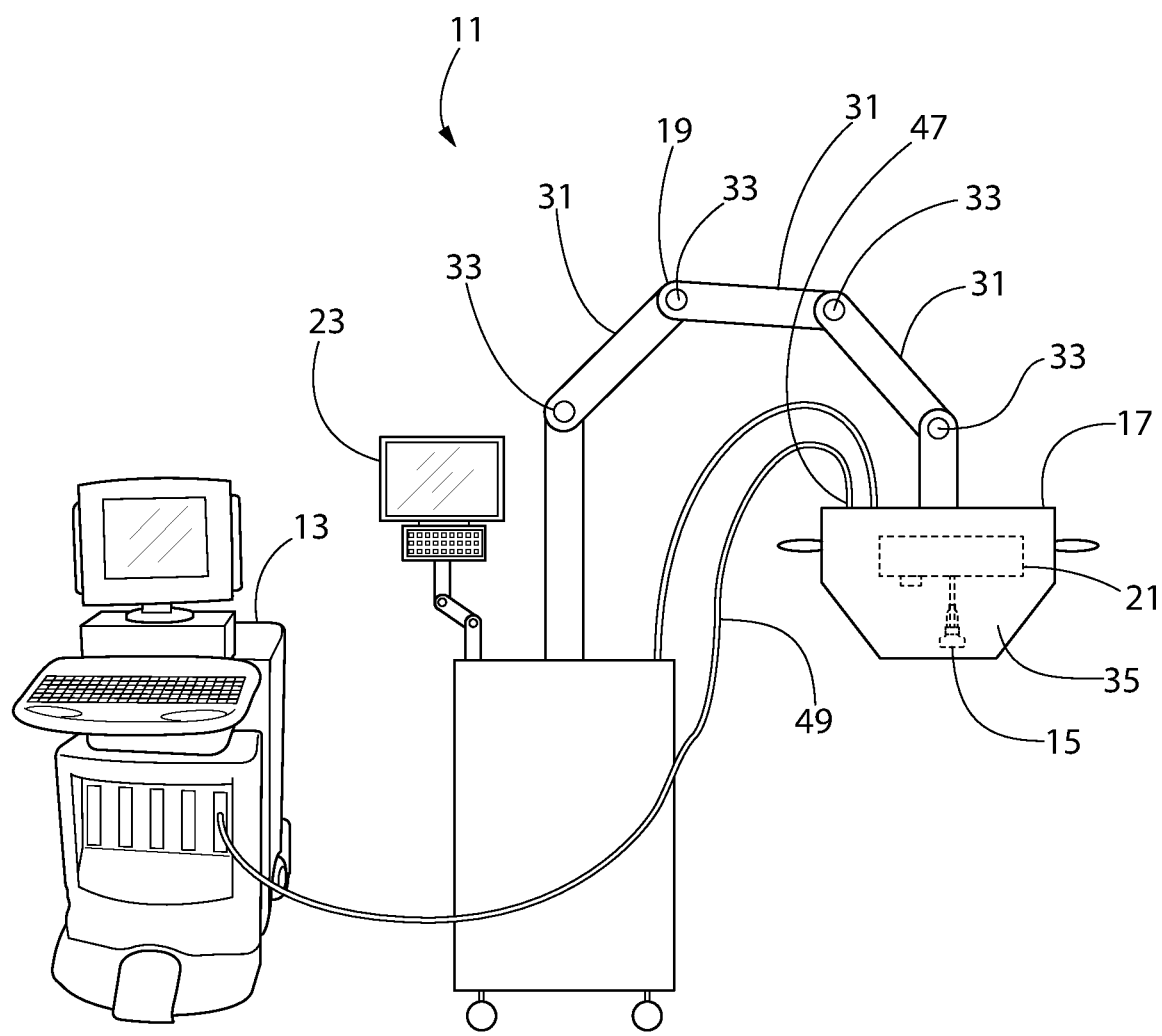
FIG. 1 schematically illustrates an ultrasound scanning system for performing an ultrasound scan of cellular tissue.

Turning in detail to the drawings, FIG. 1 illustrates a system 11 for performing an ultrasound scan of cellular tissue. The system 11 includes an ultrasound scanning device 13, which includes an ultrasound probe 15 and is configured to generate a plurality of cross-sectional images of cellular tissue. Unless otherwise indicated in the claims, the ultrasound scanning device 13 may be of a type that is known in the art, which includes a programmable processor, a volatile memory, a non-volatile memory, and programming which is used by the programmable processor to control the ultrasound probe 15, collect ultrasound scan data from the ultrasound probe 15, and to display the ultrasound scan data as images in a desirable format. The processing of ultrasound scan data is described in further detail below.

The ultrasound probe 15 is disposed within the probe enclosure 17, which is supported by an armature 19. The probe enclosure 17 is moved by the armature 19 into a position adjacent to the cellular tissue, and within the probe enclosure 17, a probe positioning assembly 21 supports and moves the ultrasound probe 15 to generate the cross-sectional images.

Both the armature 19 and the probe positioning assembly 21 may be controlled by a programmable controller 23. In addition, the programmable controller 23 may be operatively coupled to the ultrasound scanning device 13 so that programmable controller 23 may control acquisition of the cross-sectional images by coordinating image acquisition with movements of the armature 19 and the positioning assembly 21. The programmable controller 23 includes a processor, a volatile memory, and a non-volatile memory, and it may also include a display screen for viewing of the cross-sectional images generated during the screening process. Optionally, a single programmable device, such as a generic computing device, may be programmed with the same functionality of both the programmable processor of the ultrasound scanning device 13 and the programmable controller 23. As another option, the cross-sectional images may be communicated to another computing device for later viewing.

By having the programmable controller 23 control the ultrasound scanning device 13 the programmable controller 23 may be used to acquire the cross-sectional images across a plurality of scan rows such that each cross-sectional image in a one of the scan rows is substantially aligned with another of the cross-sectional images in an immediately adjacent scan row. By having substantially aligned cross-sectional images across adjacent scan rows, the cross-sectional images in adjacent scan rows may be stitched together for later viewing and review by a qualified individual. A single programmable device to perform all functions would also present these same advantages.

The armature 19 includes a plurality of articulated arm sections 31, each affixed to adjacent arm sections 31 by respective joints 33. The armature 19 may be configured to be manually operated by a user, or alternatively it may be configured to be controlled through programming of the controller 23. For embodiments in which the armature 19 is manually positioned by a user, each joint 33 may include elements which resist movement through mechanical friction, thereby helping to ensure that the armature 19, and thus the probe enclosure 17, does not move from a set position once the probe enclosure 17 is moved to be adjacent the cellular tissue to be screened. For embodiments in which the position of the armature 19 is controlled through programming of the programmable controller 23, each joint may include or be coupled to one or more servo motors, which are operatively coupled to the programmable controller 23. In such an embodiment, the servo motors may serve to stabilize the armature 19 in a fixed position, and they may be actuated by the programmable controller 23 to move the armature 19, and thus the probe enclosure 17, into position adjacent the cellular tissue to be screened. Articulated arms of both the manual and automated type are generally well known to those of skill in the art, and thus a particular implementation of the armature 19 is a matter of design choice.

The armature 19, as shown, is affixed to mobile a base 33, which serves to counterbalance the armature 19 and provide stabilization for the probe enclosure 17 during use. Alternatively, the armature 19 or the base 33 may be affixed to any appropriate anchor point, such as a floor or a wall of a building, to eliminate the need to use the base as a counterbalance.

Figure 2:
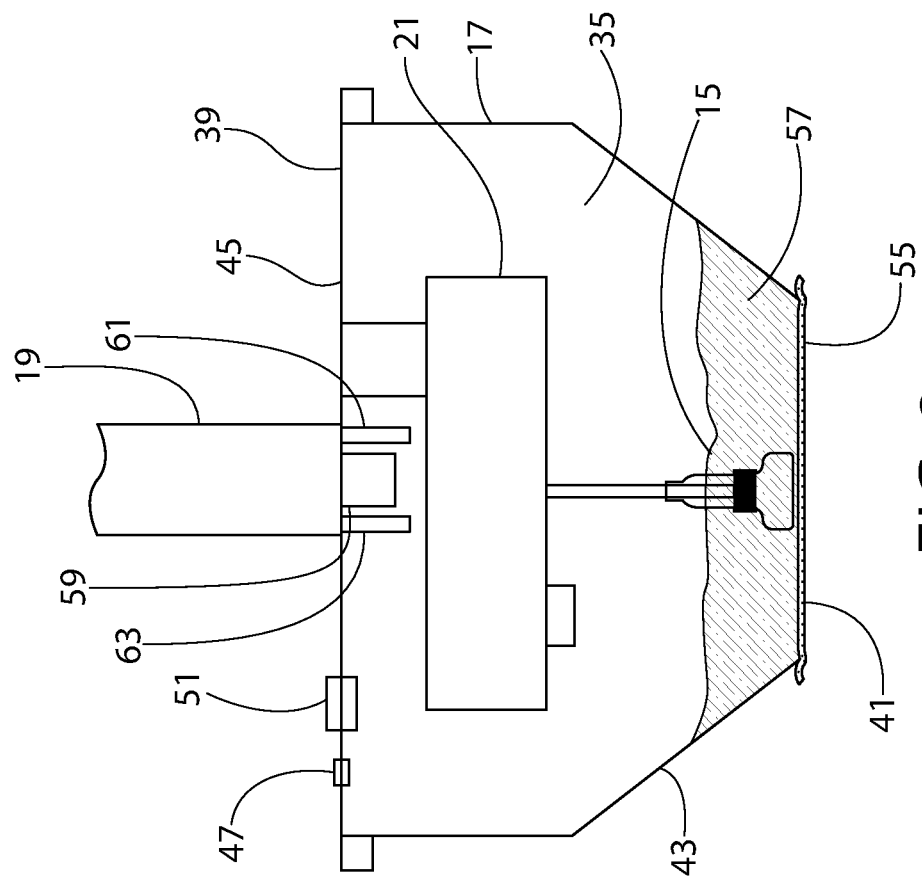
FIG. 2 schematically illustrates the probe enclosure for the system of FIG. 1.

The probe enclosure 17 is shown in FIG. 2 in schematic cross section to also show part of the interior space 35. The probe enclosure 17 is formed by a container 37 which includes a top wall 39, a bottom wall 41, and one or more side walls 43 to wholly enclose the interior space 35. The side walls 43 have a wider upper portion and taper in an angled bottom portion toward the bottom wall 41. When the system is used for screening breast tissue, the tapering in the angled bottom portion enables the enclosure to be lowered onto breast tissue of a patient without hitting the patient's head.

The container 37 is both sealable and pressurizable, and it is constructed to contain a fluid, in the form of one or more of a gas, a gel, or a liquid, under a pressure greater than atmospheric pressure without losing containment of the fluid. The container 37 may include one or more sealable entry points, with at least one of the sealable entry points being sized to permit the ultrasound probe to be inserted into the enclosure. In the embodiment shown, the top wall 39 of the container 37 may be a lid 45 which forms one of the sealable entry points to provide access to the interior space 35 of the probe enclosure 17. The lid 45 may be affixed to the sidewalls 43 with clamps, with a seal, such as a gasket, positioned between the lid 45 and the sidewalls to provide a pressure seal when the lid 45 is fully seated. Having the top wall 39 in the form of a lid 45 to serve as one of the sealable entry points also permits access to the probe positioning assembly 21 for purposes of inserting and/or servicing the probe positioning assembly 21. The probe positioning assembly 21 may be directly coupled to the lid 45, or it may be coupled to one or more of the sidewalls 43.

Another sealable entry point is shown as cable port 47, which permits a cable 49 to extend outside of the probe enclosure 17. The cable 49 may be used to carry data from the ultrasound probe 15, this data being collected by the ultrasound scanning device 13, and to carry control signals from the programmable controller 23 to the probe positioning assembly 21. Of course, these two functions may be carried on separate cables, in which case each cable may include its own separate cable port 47. Additional cable ports may be added in the event additional cables are needed to carry data, control signals, or power into or out of the interior space 35 of the probe enclosure 17.

Another sealable entry point is in the form of a pressure valve 51 which enables both pressurization of the interior space 35 of the probe enclosure 17 and pressure release of an already pressurized interior space. Alternatively, the pressurization and pressure release functions may be separated into separate valves, During use of the system 11, the pressure valve 51 is coupled to pressure source which is able to increase the pressure within the interior space 35 of the probe enclosure 17.

The bottom wall 41 of the probe enclosure 17 is formed by a flexible membrane 55, which is sonolucent and impermeable to the fluid 57 used within the probe enclosure 17. The flexible membrane 55 is affixed to the sidewalls 43 of the probe enclosure 17 in a manner consistent with the containment of the fluid 57 in the interior space 35 at an internal pressure above atmospheric pressure. In addition, the flexible membrane 55 is preferably affixed to the sidewalls 43 in such a way that it can be easily removed and replaced with a new flexible membrane. As is discussed in greater detail below, the flexible membrane 55 is displaced inwardly into the interior space 35 when the probe enclosure 17 is moved adjacent the cellular tissue to be screened.

The fluid 57 within the probe enclosure 17 is also conductive/transmissive to ultrasound, and enough of the internal volume of the interior space 35 is filled with the fluid 57 to keep the ultrasound probe submerged under the surface of the fluid 57 during screening procedures. When the system is used for screening breast tissue, in order to perform breast tissue screening on a sufficiently large percentage of the female population, the membrane preferably has about a 17 inch diameter. For other applications, the flexible membrane 55 may have a larger or smaller diameter. In certain embodiments, the fluid 57 may be gas from the surrounding atmosphere. In such embodiments, the material for the flexible membrane 55 should be selected as one which minimizes reflections of ultrasound at the fluid-air boundary. In certain other embodiments, the fluid may be contained with a pad set against the flexible membrane 55, with the ultrasound probe set against the pad during the screening process. In such an embodiment, the pad may be deformed by movement of the ultrasound probe during the screening process without causing deformation in the cellular tissue being screened.

In still other embodiments, the probe enclosure may include an intermediate plate dividing the interior space of the probe enclosure into an upper cavity and a lower cavity. In such an embodiment, the lower cavity would be disposed between the membrane and the flexible membrane. The intermediate plate would be conductive/transmissive to ultrasound energy, and the lower cavity would include a fluid that is conductive/transmissive to ultrasound energy. Further, the lower cavity could be pressurized without the need to pressurize the upper cavity (a pressure valve may be included in the intermediate plate to allow for pressurization of the lower cavity separately from the upper cavity). The ultrasound probe would be moved within the upper cavity, and may be moved under control of the programmable processor. An gel could be on, or a pad impregnated with a gel could be adjacent, the intermediate plate within the upper cavity, and the ultrasound probe could move along the surface of the intermediate plate during the screening process. Such an embodiment would ensure that the ultrasound probe does not come into contact with the flexible membrane during the screening process, and it could eliminate the need to create a 3-dimensional map of the deformed flexible membrane and/or to monitor the position of the ultrasound probe along the z-axis.

Figure 3:
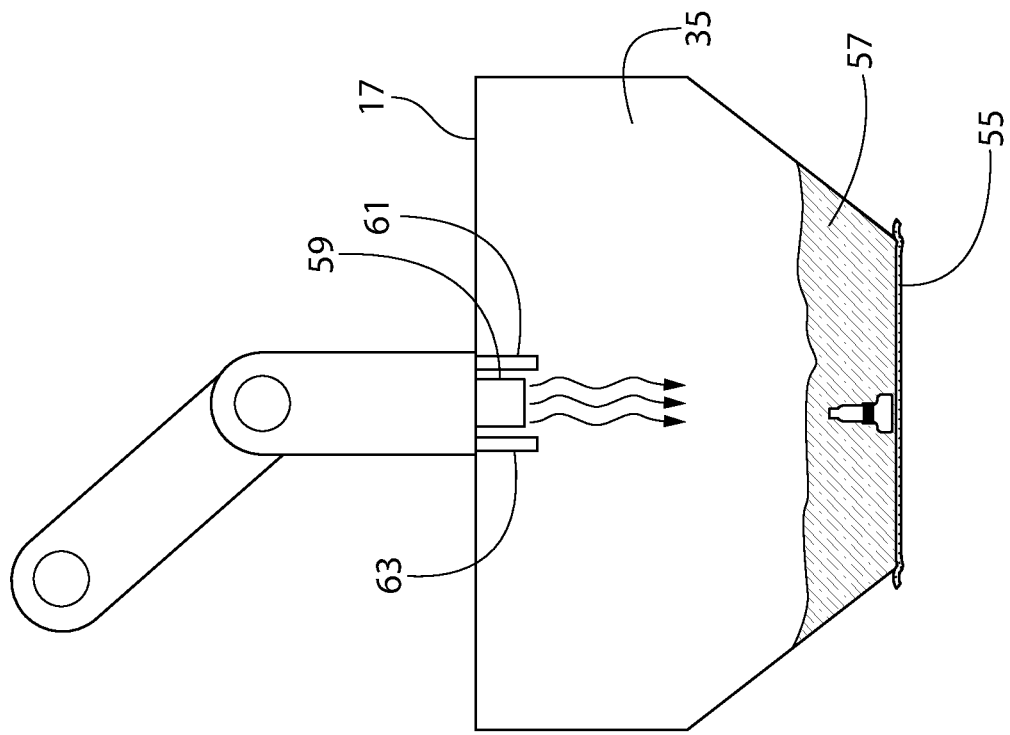
FIG. 3 schematically illustrates a probe enclosure with a heater in the interior space.

A heater 59 may also be included within the interior space 35 of the probe enclosure 17, as shown in FIG. 3. The heater 59 may be used to heat the fluid 57 to a temperature that is more comfortable to a patient when the probe enclosure 17 is moved adjacent the cellular tissue to be screened and the flexible membrane 55 is placed into contact with the cellular tissue.

A light source 61 and a camera 63 may also be included within the interior space 35 of the probe enclosure 17. Both the light source 61 and the camera 63, when included, are operatively coupled to the programmable controller 23 so that the programmable controller 23 may control the functionality of both. The light source 61 may be used to create a grid on the flexible membrane 55 so that the contours of the flexible membrane 55, when displaced by the cellular tissue to be screened, may be imaged by the camera 63 and then determined by the programmable controller 23. In this manner, the programmable controller 23 may create a 3-dimensional map of the displaced flexible membrane 55. Pressurization of the probe enclosure 17 serves to maintain the displacement of the flexible membrane 55 during the screening process, so that the programmable controller 23 may automatically maintain the head of the ultrasound probe 15 at a predetermined distance from the displaced flexible membrane 55 during the entire screening process. In alternative embodiments, the programmable controller 23 may maintain the head of the ultrasound probe 15 within a fixed plane along the z-axis, with the fixed plane having a predetermined distance as its closed distance to the cellular tissue—in other words, the fixed plane does not intersect the displaced flexible membrane 55. In such embodiments, the programmable controller 23 may use the 3-dimensional map of the displaced flexible membrane 55 to determine the positioning of the fixed plane along the z-axis.

The grid may be generated in different techniques. By way of example, one or more lasers may be used to generate a rectilinear grid of laser light on the displaced flexible membrane 55. By way of another example, the flexible membrane 55 may be coated with a dye, ink, or other material in a rectilinear pattern, such that the dye, ink, or other material reflects the wavelength of the light source 61 to render the rectilinear pattern visible to the camera 63. By way of yet another example, the individual/technician operating the system during the screening process may manually view the rectilinear grid and create a 3-dimensional map. Other methods of determining the contours of the displaced flexible membrane 55 may also be used.

During screening procedures, it may be desirable to pressurize the interior space 35 of the probe enclosure 17 so that about 1-2 psi of pressure is exerted on the tissue by the cellular tissue to be screened. Pressurizing the interior space 35 of the probe enclosure 17 serves to immobilize the cellular tissue, thereby enabling the scanning process to proceed more rapidly and in a more repeatable manner.

The repeatability of the screening process is in part due to not contacting the flexible membrane 55 or the cellular tissue with the head of the ultrasound probe 15. As one of skill in the art will recognize, when the head of an ultrasound probe touches cellular tissue being screened, it displaces the cellular tissue. Displacement of the cellular tissue during the screening process produces distortions of the cellular tissue, thereby reducing the repeatability of the screening process itself. In contrast, in the present system 11, the ultrasound probe 15 does not compress or deform the cellular tissue being screened during the imaging process, and since the cellular tissue is substantially uniformly compressed by the flexible membrane 55 and the pressure established within the probe enclosure 17, thus holding the cellular tissue firmly in place, the resulting cross-sectional images do not show distortion from the head of the ultrasound probe 15 that is typically seen in ultrasound images of the prior art.

Figure 4:
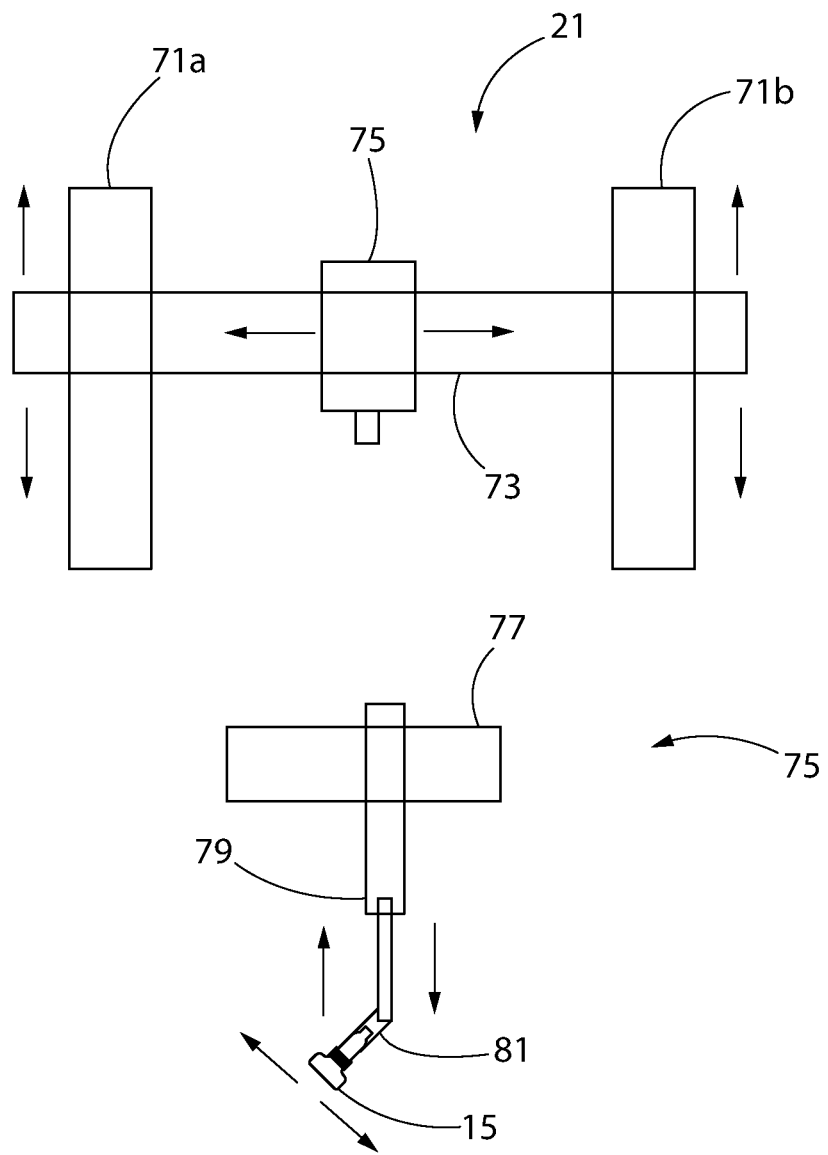
FIG. 4 schematically illustrates the probe positioning assembly for the system of FIG. 1.

As shown in FIG. 2, the probe positioning assembly 21 is also enclosed within the probe enclosure 17, and operative parts of an embodiment of the probe positioning assembly 21 are shown in FIG. 4. The probe positioning assembly 21 provides the attached ultrasound probe 15 with five degrees of freedom. Of course, depending upon the intended use of the system 11, the probe positioning assembly 21 may be constructed to provide more or fewer degrees of freedom.

The probe positioning assembly 21 is configured to translate the ultrasound probe 15 along an x-axis and a y-axis within the probe enclosure 17, the x- and y-axes being in a plane parallel to the bottom wall 41 of the container 37. In addition, the probe positioning assembly 21 may also be configured to translate the ultrasound probe 15 along a z-axis, which is perpendicular to the plane of the x-y axes. The probe positioning assembly 21 is also configured to move the ultrasound probe 15 angularly in one or two angular dimensions. When the system is used for screening breast tissue, the probe positioning assembly 21 preferably enables movement of the ultrasound probe 15 by up to 12 inches along each of the x-axis and the y-axis. In addition, when the system is used for screening breast tissue, the probe positioning assembly 21 preferably enables angular movement of the ultrasound probe 21, in both pitch and roll, by up to about 120°, or about 60° in either direction away from the vertical z-axis, which may serve as the starting position for angular rotation.

In the embodiment of FIG. 4, the probe positioning assembly 21 includes first tracks 71a, 71b which drives and translates the ultrasound probe 15 along the x-axis, and a second track 73 which drives and translates the ultrasound probe 15 along the y-axis. The first tracks 71a, 71b may be affixed to the lid 45 of the probe enclosure 17 or to the armature 19 itself. The second track 73 is coupled to the first tracks 71a, 71b so that the second track 73 itself is translated by and along the first tracks 71a, 71b. Mechanisms for precision translation of a mechanical structure are generally well known to those of skill in the art, and thus particular implementations of the first and second tracks 71a, 71b, 73 are a matter of design choice. For example, one or both of the first and second tracks 71a, 71b, 73 may drive translation through the use of a lead screw coupled to a drive motor, with the drive motor being controlled by the programmable controller 23. By way of another example, the one or both of the first and second tracks 71a, 71b, 73 may drive translation through the use of a bearing support mounted to slide on a rod, and a drive wire coupled to the bearing mounting and to a drive motor, with the drive motor being controlled by the programmable controller 23. Other types of translation mechanisms may also be used, without limitation, unless otherwise indicated herein. Those of skill in the art will, however, recognize that advantages are obtained through the use of drive mechanisms which can be quickly adjusted while at the same time minimizing vibrations introduced to the ultrasound probe 15 during the image acquisition process.

The ultrasound probe 15 is coupled to a probe mount 75, which is coupled to the second track 73. The probe mount 75 drives and translates the ultrasound probe 15 along the z-axis. Mechanisms for precision translation of a mechanical structure in along a z-axis are generally well known to those of skill in the art, and thus a particular implementation for the translation function of the probe mount 75 is a matter of design choice. For example, the probe mount 75 may include a mounting structure 77, which is coupled to the second track 73, and a piston structure 79, which is coupled to the mounting structure 77. The piston structure 79 moves with respect to the mounting structure 77 to translate the ultrasound probe 15 along the z-axis. Movement of the piston structure 79 with respect to the mounting structure 77 may be accomplished by, for example, a rack and pinion arrangement and a drive motor coupled to the pinion, with the drive motor being controlled by the programmable controller 23. Other types of translation mechanisms for translating the ultrasound probe along the z-axis may also be used, without limitation, unless otherwise indicated herein.

The probe mount 75 also includes an angular movement arm 81 coupled to the second track 73. The angular movement arm 81 rotates about at least one axis to adjust the angular position of the ultrasound probe 15. One axis may be a pitch axis, and adjustment of the angular movement arm 81 with respect to the pitch axis would rotate the ultrasound probe 15 forward and backward with respect to the second track 73. Another axis may be a roll axis, and adjustment of the angular movement arm 81 with respect to the roll axis would rotate the ultrasound probe 15 from a left side to a right side with respect to the second track 73. The pitch axis and the roll axis are orthogonal to each other, and both are parallel to the plane of the x-y axes defined by the probe positioning assembly 21. For purposes of implementation, it may be convenient to have the pitch axis aligned with the x-axis and the roll axis aligned with the y-axis of the probe positioning assembly 21. Mechanisms for precision rotation of a mechanical structure around one or more rotational axis are generally well known to those of skill in the art, and thus a particular implementation for the rotation function of the probe mount 75 is a matter of design choice. For example, the angular movement arm 81 may be coupled to one or more motors, each of which rotates the angular movement arm 81 about an axis, and the one or more motors may be controlled by the programmable controller 23.

Although the probe positioning assembly 21 is described above as having separate mechanical features which translate the ultrasound probe 15 linearly and rotate the ultrasound probe angularly, one of skill in the art will appreciate that two or more of the separate mechanical features may be combined into a single mechanical element which provides translation along multiple axes and/or multiple angular rotations. For example, the probe positioning assembly 21 may be implemented as an articulating arm that provides translation along the x-, y-, and z-axes. Alternatively, the x-y coordinate system implied by an x-y plane may be translated into a radial coordinate system, and the probe positioning assembly 21 may be implemented to reflect the use of a radial coordinate system, while still translating the ultrasound probe 15 along x- and y-axes.

FIGS. 5A-5B illustrate an alternative embodiment for a probe positioning assembly 101. In this embodiment, a first track 103 which drives and translates the ultrasound probe 15 along the x-axis, and a second track 105 which drives and translates the ultrasound probe 15 along the y-axis. The first track 103 may be affixed to the lid 45 of the probe enclosure 17 or to the armature 19 itself. The second track 105 is coupled to the first track 103 so that the second track 105 itself is translated by and along the first track 103. Again, mechanisms for precision translation of a mechanical structure are generally well known to those of skill in the art, and thus particular implementations of the first and second tracks 103, 105 are a matter of design choice. For example, one or both of the first and second tracks 103, 105 may drive translation through the use of a lead screw coupled to a drive motor, with the drive motor being controlled by the programmable controller 23. By way of another example, the one or both of the first and second tracks 103, 105 may drive translation through the use of a bearing support mounted to slide on a rod, and a drive wire coupled to the bearing mounting and to a drive motor, with the drive motor being controlled by the programmable controller 23. Other types of translation mechanisms may also be used, without limitation, unless otherwise indicated herein.

The ultrasound probe 15 is coupled to a probe mount 111, which is coupled to the second track 105. The probe mount 111 includes an articulated arm 113 with arm segments 115a-115d for driving and translating the ultrasound probe 15 along the z-axis. More or fewer arm segments may be used, as a matter of design choice. Each arm segment 115a-115d is pivotably coupled to adjacent arm segments 115a-115d. The first arm segment 115a is coupled to the to the second track 105 and pivotably coupled to the second arm segment 115b, which is also pivotably coupled to the third arm segment 115c. The third arm segment 115c is pivotably coupled fourth arm segment 115d, which is also coupled to the angular movement arm 117. The pivot coupling between the third and fourth arm segments 115c, 115d may be used to define a pitch axis for the ultrasound probe, so that pivoting of the fourth arm 115d, with respect to the third arm 115c, adjusts the angular position of the ultrasound probe about the pitch axis.

The articulated arm 113 is controlled through programming of the programmable controller 23, and each arm segment 115a-115d may include or be coupled to one or more servo motors, which are operatively coupled to the programmable controller 23. In such an embodiment, the servo motors are actuated by the programmable controller 23 to adjust the articulated arm 113 so that the ultrasound probe 15 is translated in at least the z-axis. Articulated arms are generally well known to those of skill in the art, and thus a particular implementation of the articulated arm 113 is a matter of design choice.

The angular movement arm 117 is coupled to the fourth arm segment 115d at a yoke 119 which permits angular motion of the angular movement arm 117 about the pitch and roll axes. The yoke 119 is formed by three extendable elements 121 coupled between the fourth arm segment 115d and a mounting plate 123 for the ultrasound probe 15. The extendable elements 121 are coupled to the mounting plate 123 in a triangular formation, so that a center of the triangle effectively becomes a center of rotation for the mounting plate 123, and thus also for the attached ultrasound probe 15. Each extendable element 121 is adjustable in length and can be controlled to extend or retract to cause rotation of the ultrasound probe 15 about one or both of the pitch and roll axes.

Mechanisms that may be used for each extendable element 121 are generally well known to those of skill in the art, and thus a particular implementation for the extendable elements 121 is a matter of design choice. For example, each extendable element 121 may include a lead screw coupled to a drive motor, with the drive motor being controlled by the programmable controller 23.

Figure 6B:
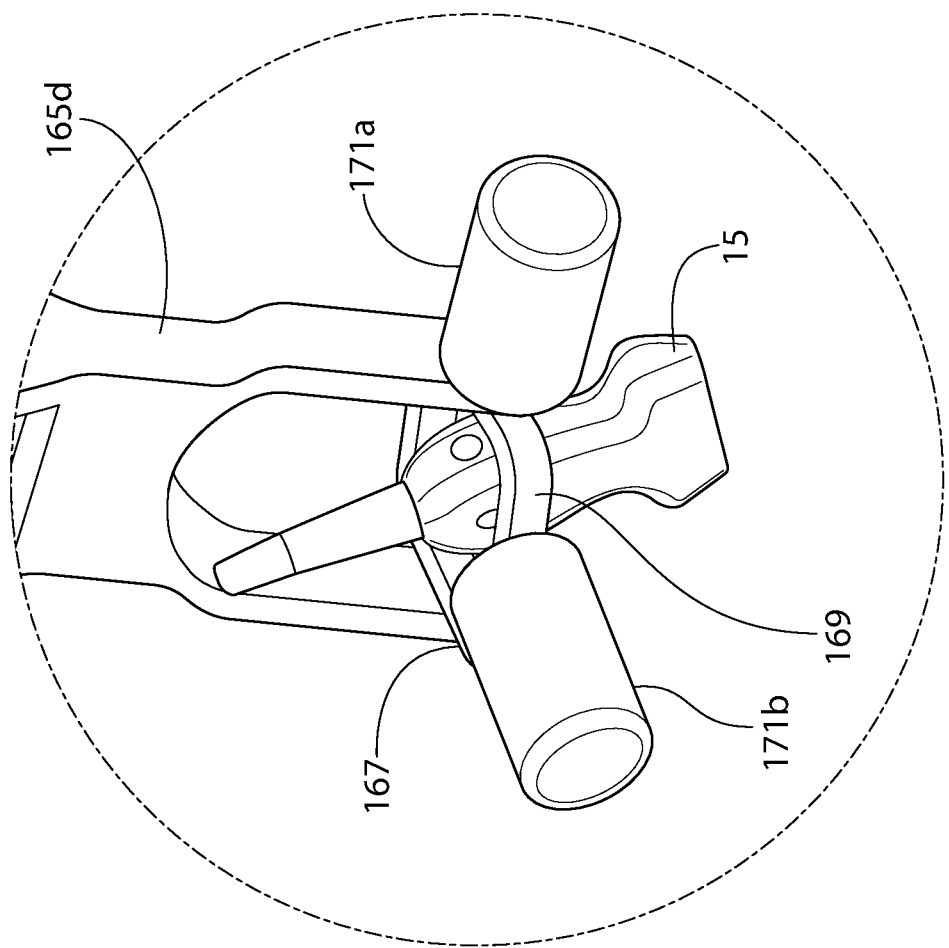
FIG. 6B is a detailed view of the probe support for the probe positioning assembly of FIG. 6A.
Figure 6A:
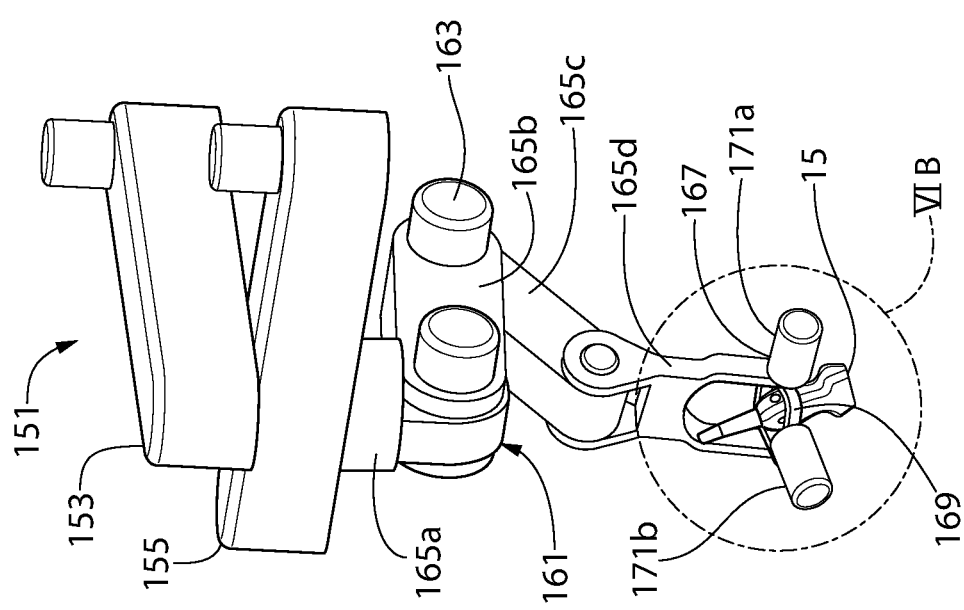
FIG. 6A is a perspective view of another probe positioning assembly for an ultrasound scanning system.

FIGS. 6A-6B illustrate another alternative embodiment for a probe positioning assembly 151. In this embodiment, a first track 153 which drives and translates the ultrasound probe 15 along the x-axis, and a second track 155 which drives and translates the ultrasound probe 15 along the y-axis. The first track 153 may be affixed to the lid 45 of the probe enclosure 17 or to the armature 19 itself. The second track 155 is coupled to the first track 153 so that the second track 155 itself is translated by and along the first track 153. Again, mechanisms for precision translation of a mechanical structure are generally well known to those of skill in the art, and thus particular implementations of the first and second tracks 153, 155 are a matter of design choice. For example, one or both of the first and second tracks 153, 155 may drive translation through the use of a lead screw coupled to a drive motor, with the drive motor being controlled by the programmable controller 23. By way of another example, the one or both of the first and second tracks 153, 155 may drive translation through the use of a bearing support mounted to slide on a rod, and a drive wire coupled to the bearing mounting and to a drive motor, with the drive motor being controlled by the programmable controller 23. Other types of translation mechanisms may also be used, without limitation, unless otherwise indicated herein.

The ultrasound probe 15 is coupled to a probe mount 161, which is coupled to the second track 155. The probe mount 161 includes an articulated arm 163 with arm segments 165a-165d for driving and translating the ultrasound probe 15 along the z-axis. More or fewer arm segments may be used, as a matter of design choice. Each arm segment 165a-165d is pivotably coupled to adjacent arm segments 165a-165d. The first arm segment 165a is coupled to the to the second track 155 and pivotably coupled to the second arm segment 165b, which is also pivotably coupled to the third arm segment 165c. The third arm segment 165c is pivotably coupled fourth arm segment 165d, which an angular movement mechanism 167. The pivot coupling between the third and fourth arm segments 165c, 165d may be used to define a pitch axis for the ultrasound probe, so that pivoting of the fourth arm 165d, with respect to the third arm 165c, adjusts the angular position of the ultrasound probe about the pitch axis.

The articulated arm 163 is controlled through programming of the programmable controller 23, and each arm segment 165a-165d may include or be coupled to one or more servo motors, which are operatively coupled to the programmable controller 23. In such an embodiment, the servo motors are actuated by the programmable controller 23 to adjust the articulated arm 163 so that the ultrasound probe 15 is translated in at least the z-axis. Articulated arms are generally well known to those of skill in the art, and thus a particular implementation of the articulated arm 163 is a matter of design choice.

The angular movement mechanism 167 includes a probe mount harness 169, which couples to the ultrasound probe 15 and enables the ultrasound probe 15 to rotate around the pitch axis and the roll axis. Two angular position control modules 171a, 171b are also coupled to the probe mount harness 169, with one angular position control module 171a placed to control rotation of the ultrasound probe 15 around the pitch axis, and the other angular position control module 171b placed to control rotation of the ultrasound probe 15 around the roll axis. Each angular position control module 171a, 171b is operatively coupled to the programmable controller 23 so that the programmable controller 23 may control the angular position control modules 171a, 171b to cause rotation of the ultrasound probe 15 about the pitch and roll axes, respectively. In certain embodiments, one or both of the angular position control modules 171a, 171b may include a servo motor.

Figure 7:
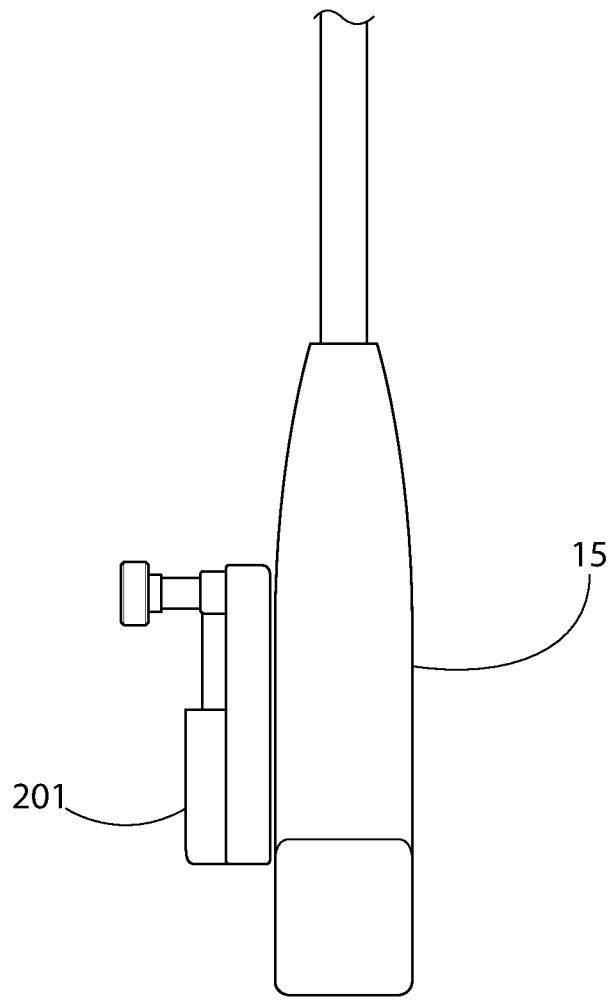
FIG. 7 illustrates probe-mounted sensors for detecting an angular position of an ultrasound probe.

An angle sensor 201 is shown affixed to the ultrasound probe 15 in FIG. 7. The angle sensor 201 is coupled to the programmable controller 23 so that the programmable controller 23 may detect the angular position of the ultrasound probe 15 during a screening process. Angular position and/or movement sensors are generally well known to those of skill in the art, and thus a particular implementation of the angle sensor 201 is a matter of design choice. In addition to the angle sensor 201, the ultrasound probe 15 and/or the probe positioning assembly (21, 101, 151) may be coupled to or include position sensors, with each position sensor coupled to the programmable controller 23 so that the programmable controller 23 may detect the angular position of the ultrasound probe 15 during a screening process. Such position sensors may track movement of the ultrasound probe 15 in any one of the degrees of freedom the probe positioning assembly (21, 101, 151) is configured to move the ultrasound probe 15. Thus, linear position sensors may be used to track movement of the ultrasound probe along any one or more of the x-axis, the y-axis, and the z-axis.

Figure 8A:
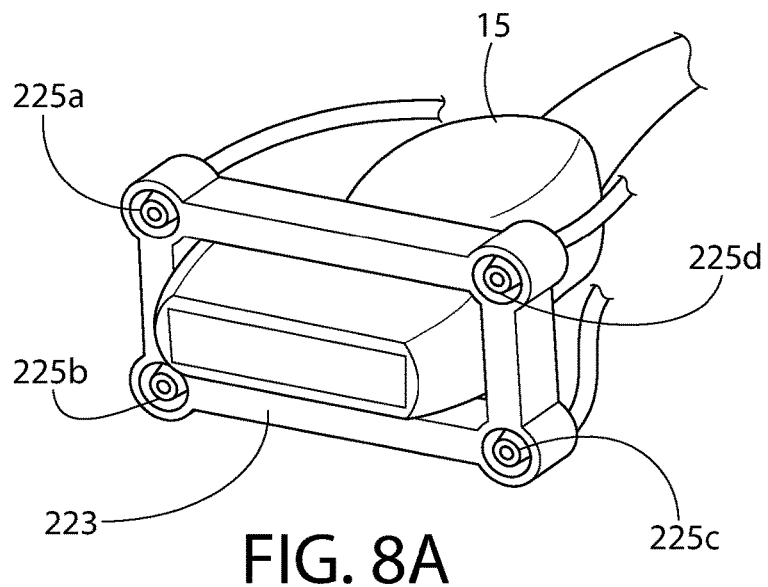
FIGS. 8A-C illustrate probe-mounted sensors for detecting the distance of an ultrasound probe from a surface.
Figures 8B, 8C:
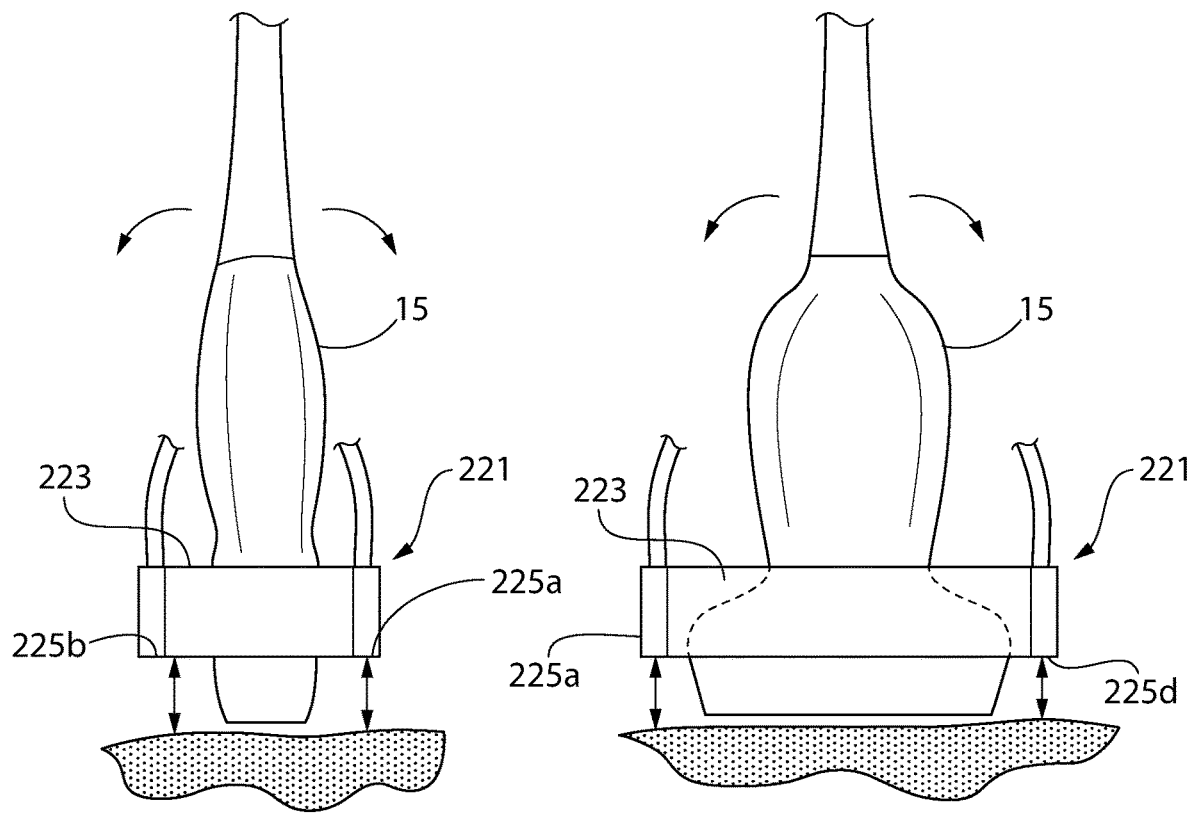

A position sensor 221 may be coupled to the ultrasound probe 15 as shown in FIGS. 8A-C. The position sensor 221 is mounted on a sensor harness 223 which is placed around the head of the ultrasound probe 15, and the position sensor 221 includes sensing elements 225a-225d, each of which is positioned at one of the corners of the sensor harness 223. While the sensor harness 223 is shown as being rectangular, it may take on any shape, and the position sensor 221 may have one or more sensor elements on the sensor harness 223. In embodiments using more than one sensing element, the sensing elements may be distributed around the head of the ultrasound probe 15. As shown, the sensing elements 225a-225d are each positioned at a corner of the sensor harness 223. Each sensing element 225a-225d measures the distance between the portion of the sensor harness 223 to which each is respectively mounted and the flexible membrane of the probe enclosure. Each sensing element 225a-225d is coupled to the programmable controller 23 so that the programmable controller 23 may detect the measured distances from the sensing elements 225a-225d.

By using the combination of the measured distances from all the sensing elements 225a-225d, the programmable controller 23 may determine whether the head of the ultrasound probe 15 is parallel or tangential to the flexible membrane within the probe enclosure, and thus to the cellular tissue being screened. The head of the ultrasound probe 15 is considered parallel to the flexible membrane when the flexible membrane under the head of the ultrasound probe 15 is planar and all sensing elements 225a-225d measure the same distance. The head of the ultrasound probe 15 is considered tangential to the flexible membrane when the flexible membrane under the head of the ultrasound probe 15 is curved and all sensing elements 225a-225d measure the same distance. When the head of the ultrasound probe 15 is not considered parallel or tangential to the flexible membrane, the programmable controller 23 may adjust the angular position of the ultrasound probe 15 by rotating the ultrasound probe 15 about at least one of the pitch axis and the roll axis. In addition, the programmable controller may use the sensing elements 225a-225d to maintain the head of the ultrasound probe 15 at a predetermined distance from the flexible membrane.

In alternative embodiments, the position sensor may include a plurality of sensing elements may be distributed on the sensing harness around the periphery of the head of the ultrasound probe, and distance measurements from each of the plurality of may be obtained by the programmable controller. The combination of the plurality of sensing elements may then be used by the programmable controller to maintain the head of the ultrasound probe at a minimum average distance from the flexible membrane.

In still other alternative embodiments, the distance of the head of the ultrasound probe 15 from the flexible membrane may be measured by other techniques, such as using capacitance, a magnetic field, ultrasound, and the like.

Figure 9A:
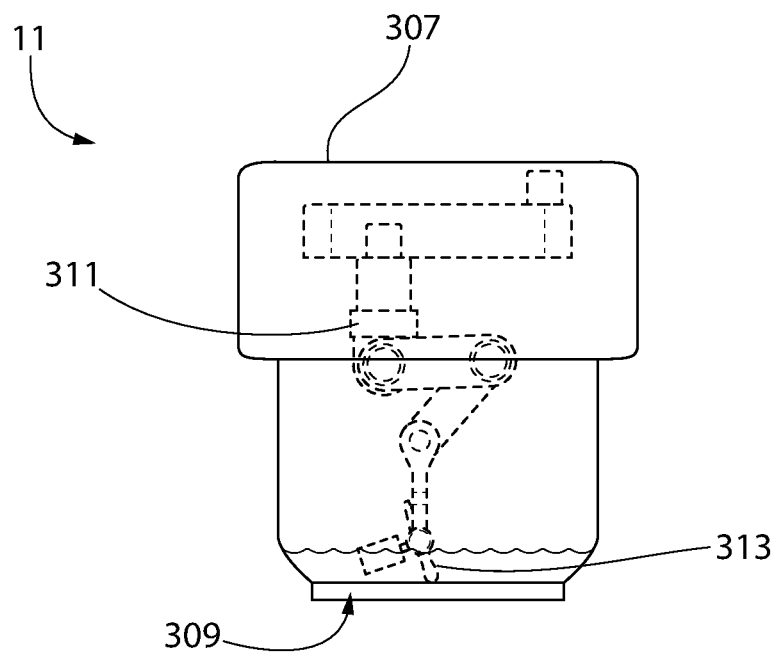
FIG. 9A illustrates a probe enclosure before being placed in position to perform an ultrasound screening.
Figure 9A:
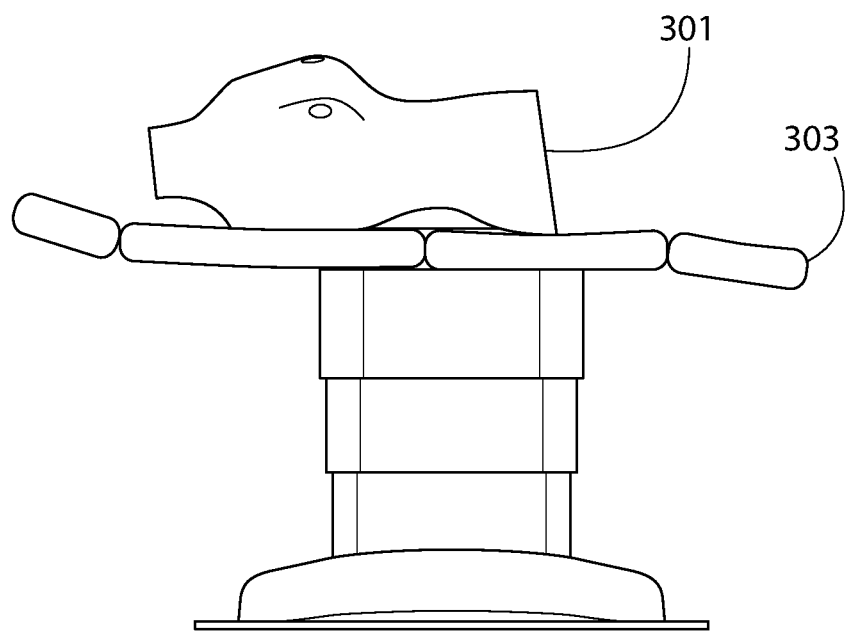
Figure 9B:
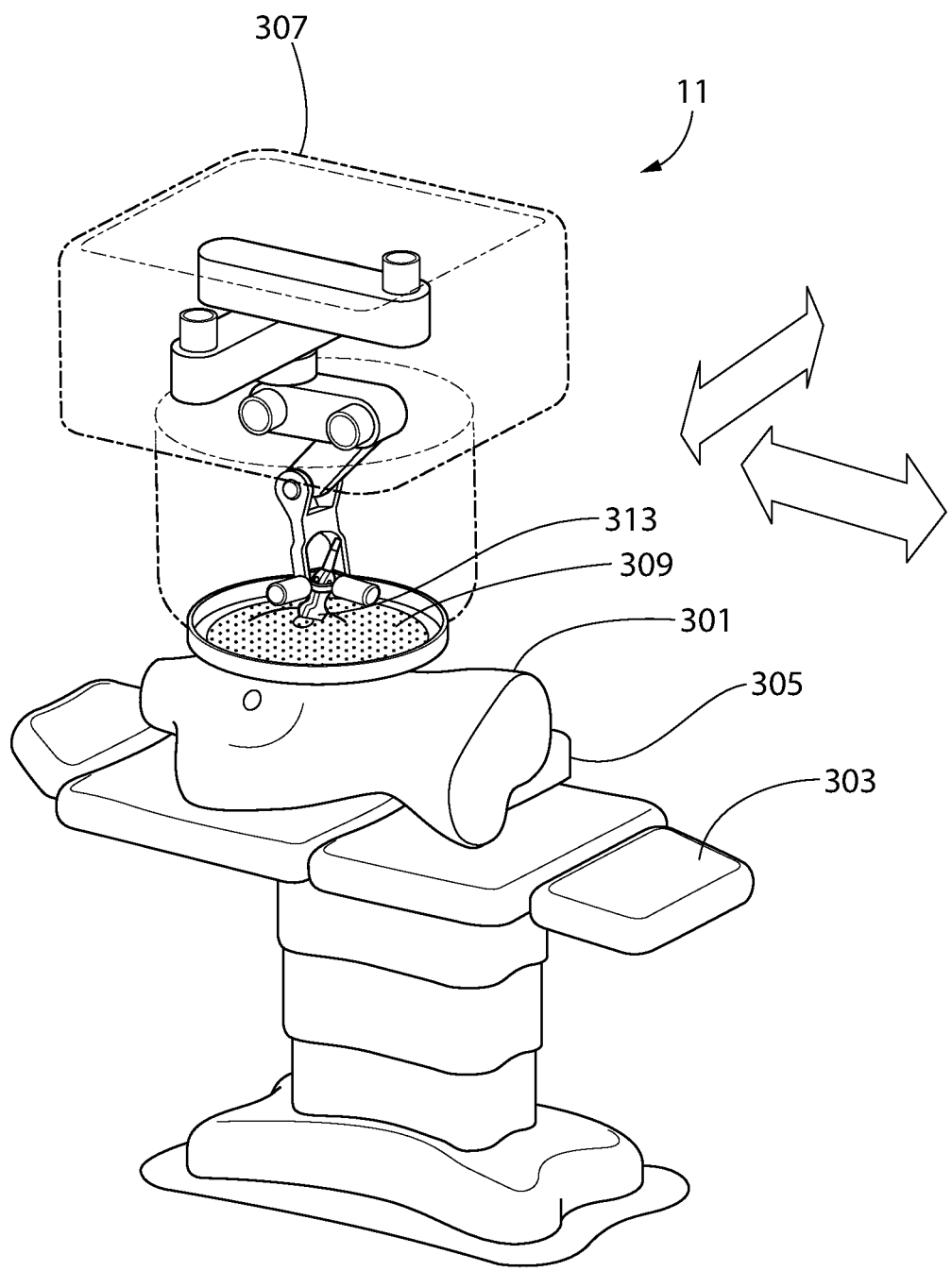
FIGS. 9B-C illustrate the probe enclosure positioned to perform an ultrasound screening.
Figure 9C:
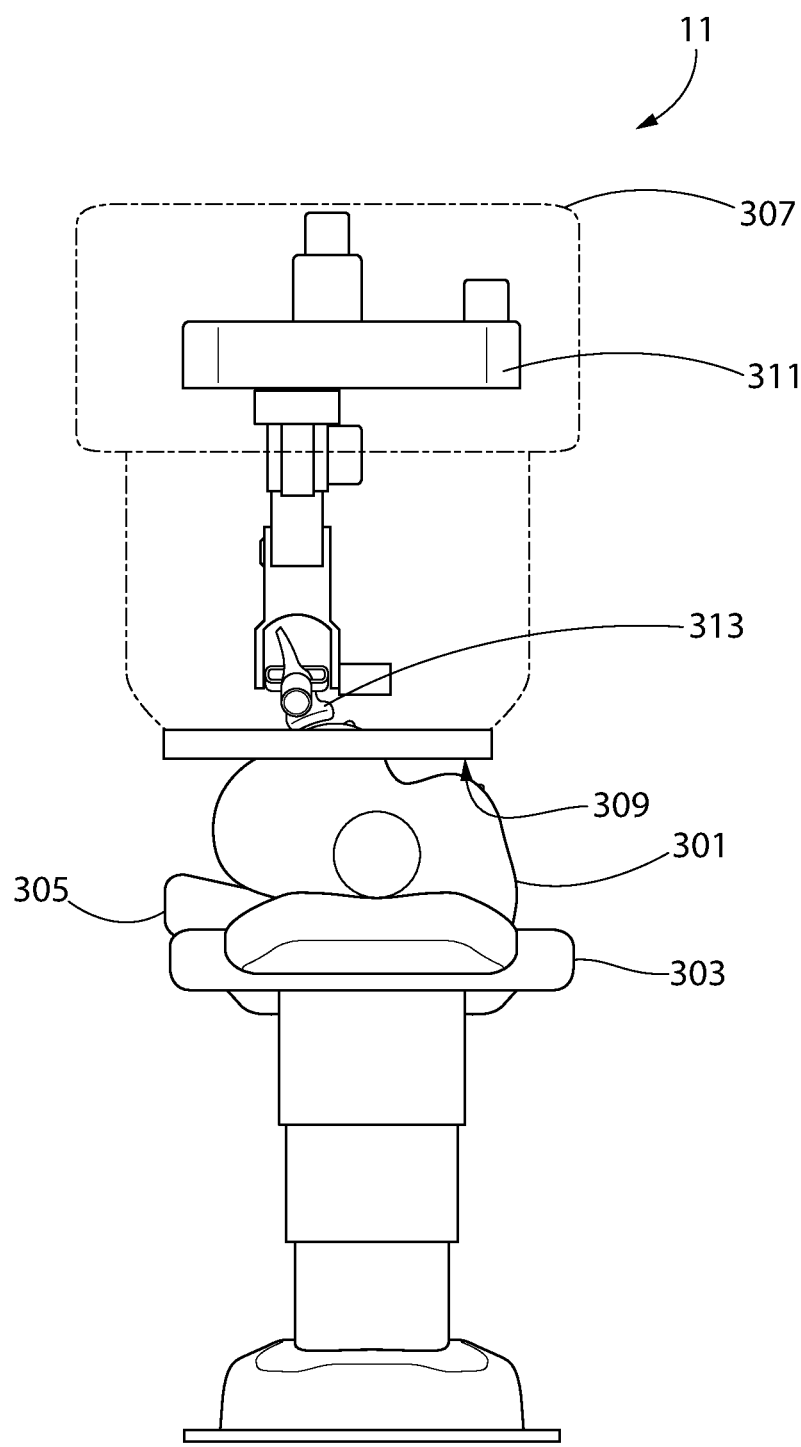

Turning to FIGS. 9A-C, basic steps of a screening process are shown within the context of the cellular tissue being screened being the breast tissue of a female. Those of skill in the art will recognize that the same steps may be readily applied to other types of cellular tissue. Also, in FIGS. 9A-C, not all parts of the system 11 are shown. Initially, the female 301 lies down on the examination couch 303 and one lateral side of her body is elevated above the other lateral side by placing a wedge 305 under her back. The lateral side of her body that is raised is the side with the breast tissue that is to be screened. As an alternative, the examination couch may be constructed to tilt along a longitudinal line that extends down the center of the examination couch, so that tilting of the examination couch effectively raises the one lateral side of her body above the other lateral side. Such a tilting examination couch may also include a tilting mechanism which includes an angle gauge. With such a tiling mechanism, the angle at which a particular patient is placed during the screening process may be noted in the patient's file, and that same angle can be used for that same patient during future screenings.

Each of the steps in the screening process described herein, starting with positioning of the probe enclosure 307, may be implemented through automation using the programmable processor. It is anticipated that the process described below may be fully automated, so that the screening process may proceed quickly and without discomfort to the female.

Figure 10:
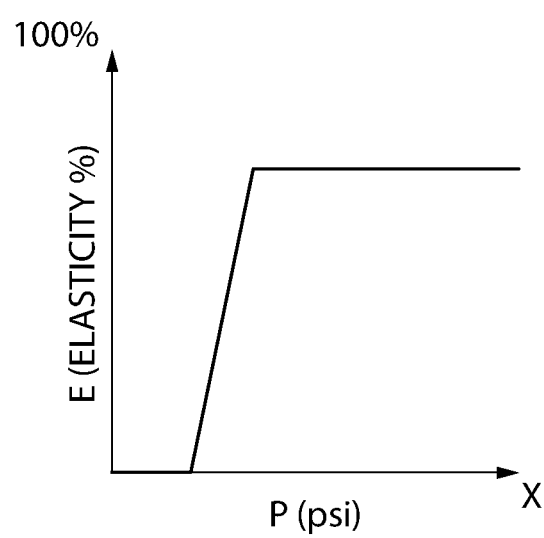
FIG. 10 illustrates an exemplary elasticity curve for a typical flexible membrane under pressure.
Figure 11A:
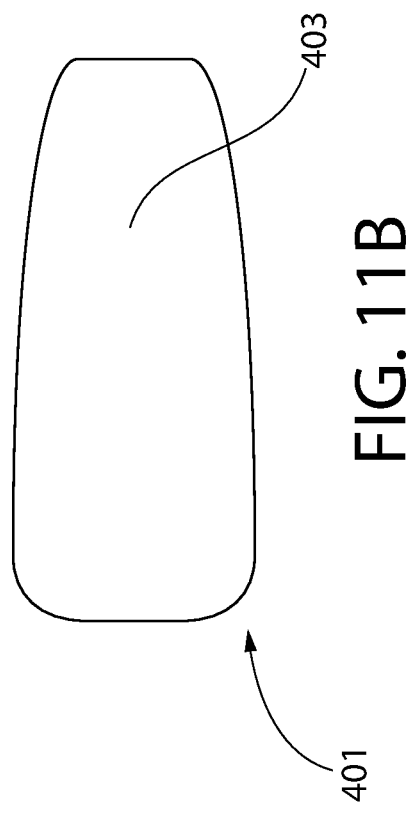
FIGS. 11A-D illustrate an axilla pad.
Figure 11B:
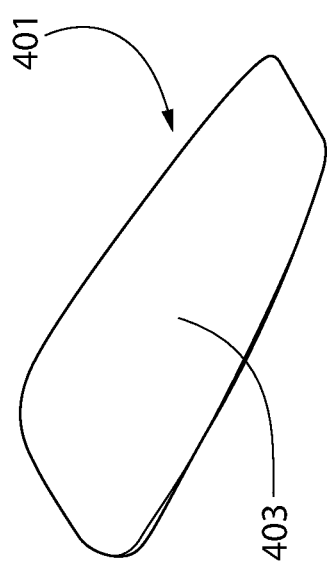
Figure 11C:
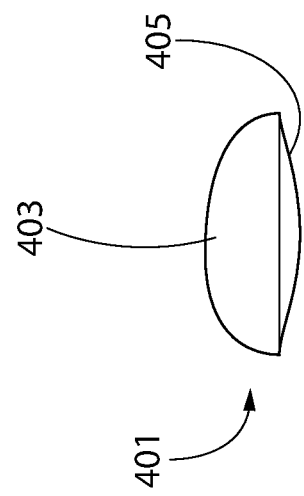
Figure 11D:
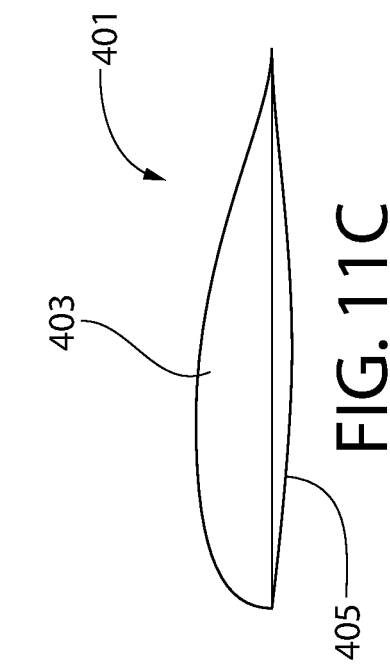

The probe enclosure 307 is placed above the breast tissue on the raised lateral side of the female's body. The fluid within the probe enclosure 307 and the flexible membrane may be heated by a heater before proceeding with the screening process. When the female is comfortably in the appropriate position, the probe enclosure 307 is lowered so that the flexible membrane 309 on the bottom of the probe enclosure 307 is placed adjacent to and displaced by the breast tissue to be screened. Once the probe enclosure 307 is in place and the flexible membrane 309 is displaced by the breast tissue, then the internal cavity of the probe enclosure 307 is pressurized. Because the flexible membrane presses against the breast tissue, it may not be necessary to place an ultrasound coupling agent between the flexible membrane and the breast tissue. Preferably, the internal cavity is pressurized to about 1-2 psi, although it may be more or less pressurized, depending upon the type of tissue being screened, the amount of displacement of the flexible membrane 309, and the resiliency of the flexible membrane. Upon pressurization of the probe enclosure 307, the edges of the flexible membrane 309 may balloon out to encompass more of the breast tissue outside of the lower diameter of the probe enclosure 307. Flexible membrane materials will exhibit an elasticity curve, and FIG. 10 shows an exemplary elasticity curve for flexible membrane materials that are suitable for use as the flexible membrane.

After the probe enclosure 307 has been pressurized, then the grid is created on the flexible membrane 309 and the grid is imaged so that the 3-dimensional map may be created for the displaced flexible membrane 309. The programmable controller is programmed to then use the 3-dimensional map of the displaced flexible membrane 309 to automate movement of the probe positioning assembly 311 so that the ultrasound probe 313 is moved along the contours of the 3-dimensional map, while maintaining the head of the ultrasound probe 313 at a predetermined distance from the flexible membrane 309. Movement of the ultrasound probe 313 may proceed in a series of scan rows, such as is known and disclosed in U.S. Pat. No. 6,524,246, the disclosure of which is incorporated herein by reference. The level of the fluid in the probe enclosure 307 should enough so that when the ultrasound probe 313 is moved, the head of the ultrasound probe 313 remains immersed under the surface of the fluid. Also, linear and angular movement of the probe should proceed while receiving feedback from the sensors that determine the distance of the head of the ultrasound probe from the flexible membrane 309. The linear and angular position of the ultrasound probe 313 may then be adjusted in response to the measured distance. In this way, the ultrasound probe 313 may remain at a predetermined from the flexible membrane 309.

Once the cross-sectional images in a series of adjacent scan rows are obtained, adjacent ones of the cross-sectional images in adjacent scan rows are stitched together to form larger cross-sectional images of the whole breast tissue. These larger cross-sectional images may then be viewed on a display screen in a manner also disclosed in U.S. Pat. No. 6,524,246.

Because the programmable controller is able to control the linear and angular movement of the ultrasound probe 313, because the contours of the flexible membrane 309, and thus the breast tissue, are known, and because the breast tissue is held firmly in place by the pressurized probe enclosure 307 and the flexible membrane 309, the screening process may proceed more quickly than with systems of the prior art, with no deformation of the breast tissue being screened being caused by the ultrasound probe. By eliminating unwanted deformation of the breast tissue during the screening process, the breast tissue maintains its form and shape during the entire screening process, thus making it so that adjacent cross-sectional images in adjacent scan rows may be stitched together for later viewing. Viewing the stitched together cross-sectional images of the whole breast tissue is much faster than viewing the cross-sectional images row by row.

Figure 12:
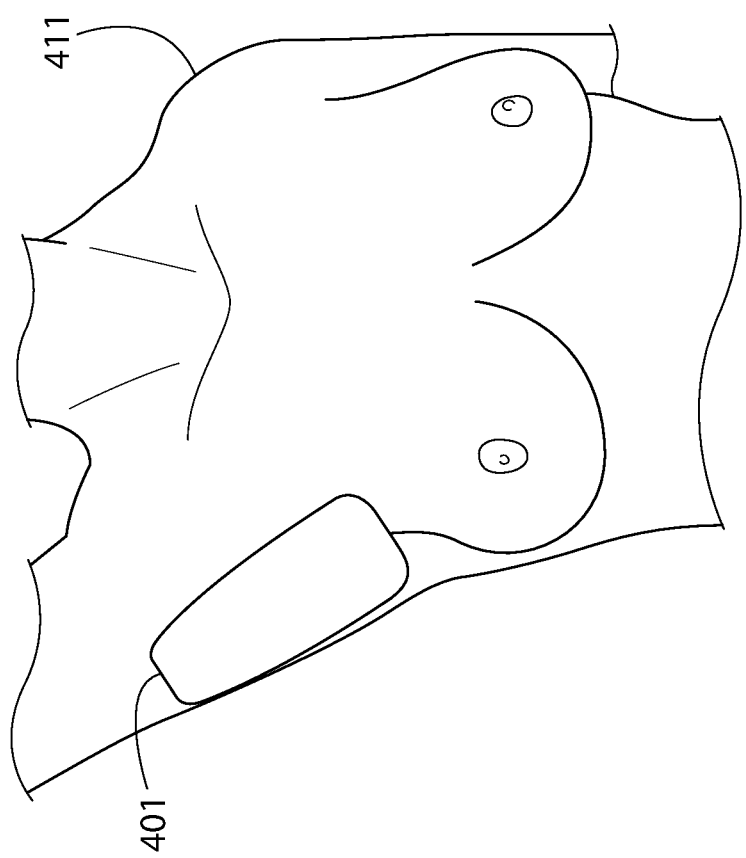
FIG. 12 illustrates placement of an axilla pad during an ultrasound screening.

Figs. IIA-D illustrate an axilla pad 401 made of solid deformable acoustical gel which is molded to fit the axilla of a patient 411. The acoustical gel is one that is conductive/transmissive to ultrasound energy. The axilla pad 401 may be advantageously used with the ultrasound scanning system to improve scan results in the vicinity of the axilla. The inward facing side 403 of the axilla pad 401, which is the side that faces the axilla of the patient when in use, is shaped to conform to the tissue of the axilla when the patient's arm is raised over the shoulder, as shown in FIG. 12. The outward facing side 405 of the axilla pad 401 is substantially flat so that a flat scanning surface is presented to the head of an ultrasound passing over the axilla pad 401 during an ultrasound scan.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A method of performing an ultrasound scan of cellular tissue comprising:
   placing a probe enclosure adjacent the cellular tissue, wherein an ultrasound probe and a first material are disposed within the probe enclosure and a bottom of the probe enclosure is formed by a flexible membrane, the first material comprising an ultrasonic coupling material, the flexible membrane and the ultrasonic coupling material being ultrasonically conductive, and wherein the flexible membrane is placed adjacent to and displaced by the cellular tissue;
   pressurizing a cavity formed by the probe enclosure to above atmospheric pressure by introducing a second material into the cavity through at least one pressure valve, the cavity being adjacent the flexible membrane, and the second material being different from the first material;
   moving the ultrasound probe within the probe enclosure over the flexible membrane, such that a head of the ultrasound probe is submerged in the ultrasonic coupling material and maintained at least at a minimum distance from the flexible membrane; and generating a plurality of cross-sectional images of the cellular tissue as the ultrasound probe moves over the flexible membrane.

2. The method of claim 1, wherein moving the ultrasound probe within the probe enclosure includes moving the ultrasound probe using a probe positioning assembly disposed within the probe enclosure.

3. The method of claim 2, wherein moving the ultrasound probe using the probe positioning assembly includes controlling the probe positioning assembly using a controller, wherein the controller is configured to be programmable.

4. The method of claim 3, wherein controlling the probe positioning assembly using the controller includes:

measuring a position of the ultrasound probe within the probe enclosure; and controlling the probe positioning assembly using the controller in response to the measured position.

5. The method of claim 4, wherein controlling the probe positioning assembly using the controller includes controlling the probe positioning assembly to maintain the head of the ultrasound probe at a predetermined distance from the flexible membrane.

6. The method of claim 1, wherein the plurality of cross-sectional images of the cellular tissue span across a plurality of scan rows, with the plurality of cross-sectional images in the scan rows being evenly spaced.

7. The method of claim 1, wherein placing the probe enclosure adjacent the cellular tissue includes heating the ultrasonic coupling material.

8. The method of claim 1, wherein placing the probe enclosure adjacent the cellular tissue includes placing an axilla pad adjacent the cellular tissue such that a flat surface of the axilla pad is adjacent the flexible membrane when the flexible membrane is placed adjacent to the cellular tissue.

9. The method of claim 1, wherein placing the probe enclosure adjacent the cellular tissue includes positioning an examination wedge under one lateral side of a patient to raise the one lateral side of the patient above the other lateral side of the patient.

* * * * *